Nov. 29, 1949. A. KREBS Plant Pat. 900
POLYANTHA ROSE PLANT
Filed Dec. 18, 1947
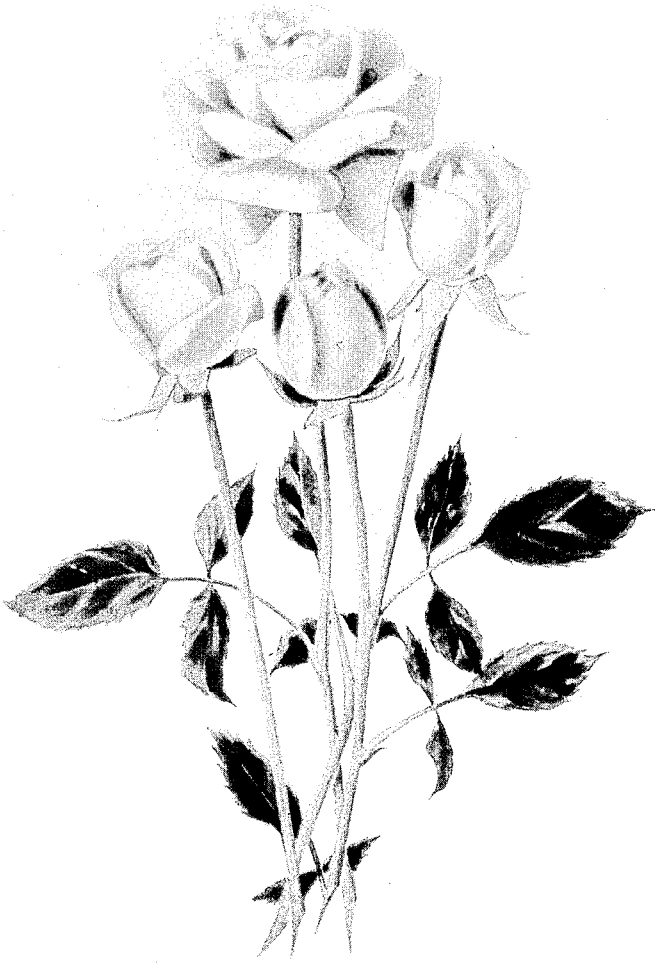
INVENTOR
Alfred Krebs
By Orville M. Kile
Plant Pat. Agt.

Patented Nov. 29, 1949

Plant Pat. 900

UNITED STATES PATENT OFFICE

900

POLYANTHA ROSE PLANT

Alfred Krebs, Montebello, Calif., assignor to
Howard & Smith, Montebello, Calif.

Application December 18, 1947, Serial No. 792,549

1 Claim. (Cl. 47—61)

My present invention relates to an improved variety of polyantha rose plant which was derived from a cross made by me, between two unnamed seedlings.

The very great vigor of growth of this variety is its most outstanding feature, since it is far more vigorous than any other known polyantha. Plants budded on yearling stock in May were 2 to 2½ feet high in November in our fields. Two-year plants, usually used for marketing, would be not less than 3 feet high, and mature plants often attain a height of 4 feet in a given season.

The variety is also outstanding because of its unusual freedom of bloom; it being absolutely remontant from early spring to late autumn.

The color and lasting ability of its flowers, together with the almost complete thornlessness of its stems, combine with these other features to make it a very desirable cut flower, aside from its value as a garden bedding rose.

The new variety has been asexually reproduced from cuttings, in the greenhouses of Howard & Smith at Montebello, California, and its characteristics appear to be permanent.

The accompanying illustrations show an open rose and three buds in various stages of opening, together with portions of the stems and foliage—all in approximately their true colors. Allowance must be made, however, for the fact that the color of the flower is somewhat variable in cool weather.

Following is a detailed description of the plant and flowers as grown in our open fields. Color nomenclature refers to the ordinary dictionary meaning except where plate references are given.

*The plant*

Growth habit: More vigorous in growth than any other known variety of polyantha rose. Two-year plants are not less than 3 feet high and, under normal conditions mature plants reach a height of four feet in a single season.

Blooming habit: Has very great freedom of bloom. Is absolutely remontant from early spring to late fall. Flowers are borne on large trusses, main basic-break stems averaging 30 blossoms. Branchlets carry an average of 10 blossoms.

Disease resistance: In this climate, the variety is immune to all diseases common to roses.

Stems:

*Color.*—Light green with reddish tinge.
*Strength.*—Very strong.
*Rigidity.*—Wiry; erect.
*Thorns.*—Practically none.

Foliage:

*Number of leaflets.*—3 to 5.
*Quantity.*—Plants well foliaged, with leaves borne up close to inflorescence.
*Aspect.*—Glossy.
*Shape.*—Long oval with moderately acute base and acuminate apex. Serrations regular but not deep.
*Size.*—Total leaf is 3½ to 4 inches in length.
*Texture.*—Leathery.
*Color.*—Green when fully developed. Reddish cast shown on new shoots.
*Leaf stem.*—Reverse pale green; upper portion deep green.

*The flower*

Bud:

*Size.*—Averages ¾ inches long when half-open.
*Shape.*—Globular.
*Color.*—Approximately Rose Red (Plate XII, Ridgway's Color Standards and Nomenclature).
*Opening.*—Opens slowly.
*Calyx and sepals.*—Smooth, simple, early-reflexing.
*Stipules.*—Almost non-existent.
*Peduncle.*—Strong and straight, though slender.

Bloom:

*Borne.*—In large trusses. Heads in branched trusses average about 12 inches in diameter.
*Size of individual flower.*—About 2 inches in diameter.
*Form.*—Full high centered, with outer petals slightly reflexed. Later opens into somewhat camellia shape.
*Color.*—Usually approximately Rose Red (Plate XII, Ridgway's), although in cool weather the color is somewhat variable from dark rose to light crimson.
*Discoloration.*—Does not discolor except under very adverse weather conditions.
*Petalage.*—Double, averaging 50 petals.
*Fragrance.*—Very faint.
*Longevity.*—Splendid keeper, especially as a cut flower.

Petals:

*Shape.*—Almost round, but slightly pointed at apex. Deeply cupped.
*Aspect.*—Satiny.
*Texture.*—Firm.
*Size.*—½ to ¾ inch in diameter.
*Persistence.*—Remain in good condition for life of flower, then drop cleanly.

*Arrangement.*—Overlapping. Evenly placed as in many camellias.

Reproductive organs:

*Pistils.*—Dull white.

*Stamens.*—Filaments dull white. Anthers light yellow. Pollen yellow.

*Fruit.*—Flowers sterile, producing practically no fruit.

Having thus disclosed my invention, I claim:

The new and distinct variety of polyantha rose plant, substantially as herein disclosed, characterized particularly by its extremely vigorous growth; its very free and completely remontant blooming habit; its very large trusses; the substantial thornlessness of its stems; its globular bud; and the excellent keeping qualities, approximately rose red color, and large petalage of its flowers.

ALFRED KREBS.

No references cited.